(12) United States Patent
Wang et al.

(10) Patent No.: US 12,226,899 B2
(45) Date of Patent: Feb. 18, 2025

(54) STRAP CONNECTOR, ROBOTIC ARM AND ROBOT

(71) Applicant: CORNERSTONE TECHNOLOGY (SHENZHEN) LIMITED, Shenzhen (CN)

(72) Inventors: Zerui Wang, Shenzhen (CN); Fengyu Cao, Shenzhen (CN)

(73) Assignee: CORNERSTONE TECHNOLOGY (SHENZHEN) LIMITED, Shenzhen (CN)

( * ) Notice: Subject to any disclaimer, the term of this patent is extended or adjusted under 35 U.S.C. 154(b) by 233 days.

(21) Appl. No.: 17/940,912

(22) Filed: Sep. 8, 2022

(65) Prior Publication Data
US 2023/0001571 A1    Jan. 5, 2023

Related U.S. Application Data

(63) Continuation of application No. PCT/CN2021/125033, filed on Oct. 20, 2021.

(30) Foreign Application Priority Data

Dec. 2, 2020   (CN) .................. 202011414092.X (51) Int. Cl.
*B25J 9/10*     (2006.01)
*B25J 9/06*     (2006.01)

(52) U.S. Cl.
CPC ..... *B25J 9/104* (2013.01); *B25J 9/06* (2013.01)

(58) Field of Classification Search
CPC ..... B25J 9/06; B25J 9/104; F16H 7/18; F16H 2007/0863; F16H 2007/0865; F16H 55/36
See application file for complete search history.

(56) References Cited

U.S. PATENT DOCUMENTS

| 4,813,292 A | 3/1989 | Boyko |
| 5,682,795 A | 11/1997 | Solomon et al. |

(Continued)

FOREIGN PATENT DOCUMENTS

| CN | 1847698 A | 10/2006 |
| CN | 208598520 U | 3/2019 |

(Continued)

OTHER PUBLICATIONS

Extended European Search Report dated Sep. 13, 2023 regarding Application No. 21899757.5.

(Continued)

*Primary Examiner* — Bobby Rushing, Jr.

(57) ABSTRACT

A strap connector, a robotic arm and a robot are provided. The strap connector includes a core, a strap and a pulley. The core includes a belly portion and a neck portion fixed to the belly portion. The neck portion has a width tapering in a direction away from the belly portion. The pulley defines a core chamber in which the core is received, the core chamber is accessible through an opening. The strap is connected to the core and extending out of the core chamber through the opening. The core chamber has two inner side walls opposing each other and extending from the opening. The neck portion is disposed closer to the opening than the belly portion. The two inner walls of the core chamber clamp the neck portion and the strap when the strap is tensioned.

20 Claims, 8 Drawing Sheets

(56) References Cited

U.S. PATENT DOCUMENTS

| | | | |
|---|---|---|---|
| 9,261,172 B2 | 2/2016 | Solomon et al. | |
| 10,595,948 B2 * | 3/2020 | Solomon | ................ A61B 34/37 |
| 2013/0160591 A1 | 6/2013 | Kent | |
| 2016/0327138 A1 | 11/2016 | Mu et al. | |
| 2018/0079074 A1 | 3/2018 | Devengenzo et al. | |

FOREIGN PATENT DOCUMENTS

| | | | | |
|---|---|---|---|---|
| CN | 211325577 U | 8/2020 | | |
| CN | 211693400 U | 10/2020 | | |
| CN | 112682483 A | 4/2021 | | |
| CN | 214743087 U | 11/2021 | | |
| EP | 0134720 B1 | 1/1987 | | |
| GB | 2088713 A * | 6/1982 | ............. | A62B 35/04 |
| SU | 1523794 A1 | 11/1989 | | |

OTHER PUBLICATIONS

International Search Report and written opinion dated Jan. 19, 2022 for International application No. PCT/CN2021/125033.

\* cited by examiner

FIG. 11 though the opening. The core chamber has two inner side walls opposing each other and extending from the opening. The neck portion is disposed closer to the opening than the belly portion. The two inner walls of the core chamber clamp the neck portion and the strap when the strap is tensioned.
STRAP CONNECTOR, ROBOTIC ARM AND ROBOT

CROSS REFERENCE TO RELATED APPLICATIONS

The present disclosure is a continuation of PCT Application No. PCT/CN2021/125033, filed Oct. 20, 2021 which claims priority to Chinese patent application No. 202011414092.X, filed Dec. 2, 2020, each of which is incorporated by reference herein in its entirety.

TECHNICAL FIELD

The present disclosure relates to the field of mechanical transmission, and particularly to a transmission structure of a robotic arm for a surgical robot.

BACKGROUND

In typical surgical robots, steel straps are employed to connect pulleys at both ends of a link of a robotic arm for motion transmission and mechanical cooperation between various structures. And steel strap connectors are provided to couple the steel straps to the pulleys, which have a significant influence on service life of the steel straps and compactness of the structures.

The existing steel strap connectors generally connect the steel straps to the pulleys through bolts and the like. For example, a steel strap is welded to a connector such as a steel block which is then inserted into a receiving groove defined by the pulley. The connector is immovable as getting stuck in the groove when the steel strap is tensioned, or is prevented from moving with being pressed by an additional bolt. Typically, the strap is overlapped on a surface of the block and fixed thereto by welding. The connection between the strap and the block is supported by merely the welds which is subjected to shear forces when the strap is tensioned.

The above existing solutions have disadvantages as follows. Firstly, the welds between the straps and the connectors are mainly subjected to shear forces, and the shear yield strength of the welds is far lower than the tensile yield strength and compressive yield strength thereof, so that the welds are fragile when subjected to shear forces compared with being subjected to tensile force. Secondly, after the steel straps and connectors are welded, the yield strength at the welds is reduced to, generally, 80% to 90%, which makes the connectors fragile. Thirdly, in order to avoid fracture due to lower shear yield strength and local reduction of the yield strength caused by welding, the straps may wrap around a pulley at a larger angle to increase a friction force between the steel straps and the pulley against the tension which causes the shear stress at the welds, so as to ensure safety of the steel straps. Fourthly, in order to ensure reliability of the welds, multiple welds with larger lengths are required to bear the shear force, which results in a large length of the steel strap connector and thus a large space occupation, while a limited space is reserved for the steel strap connector in some practical occasions. Fifthly, in order to improve the fatigue life of steel straps, each strap usually has a plurality of layers which need to be uniformly pre-tightened and wrapped on a pulley for subsequent welding, resulting in a complex process of welding between the steel strap connector and the steel strap.

SUMMARY

Embodiments of the present disclosure provide a strap connector including a core, a pulley and a strap. The core includes a belly portion and a neck portion fixed to the belly portion. The neck portion has a width tapering in a direction away from the belly portion. The pulley defines a core chamber in which the core is received. The core chamber is accessible through an opening. The strap connected to the core and extends out of the core chamber through the opening. The core chamber has two inner side walls opposing each other and extending from the opening. The neck portion is disposed closer to the opening than the belly portion. The two inner walls of the core chamber clamp the neck portion and the strap when the strap is tensioned.

The embodiments of the present disclosure further provide a robotic arm and a robot including the robotic arm. The robotic arm employs the structure of the strap connector as described above.

BRIEF DESCRIPTION OF THE DRAWINGS

To illustrate the technical solutions according to the embodiments of the present disclosure more clearly, the accompanying drawings for describing the embodiments are introduced briefly in the following. Apparently, the accompanying drawings in the following description are only some embodiments of the present disclosure, and those skilled in the art can derive other drawings from the accompanying drawings without creative efforts.

DETAILED DESCRIPTION

In the following description, several embodiments of the present disclosure are shown by example. It should be appreciated that other embodiments may be derived with changes in mechanical component, structure, electrical, and operation without departing from the spirit and scope of the present disclosure. The following detailed description is not intended to limit the present disclosure, and the scope of embodiments of the present disclosure is limited by the claims.

All directional indications (such as upper, lower, left, right, front, rear, etc.) in embodiments of the present disclosure are used only to explain relative positional relationships, motion situations, etc., between components under a particular posture (as shown in the drawings), and will change accordingly if the particular posture changes.

In that present disclosure, expressions concerning "first," "second," etc., are for descriptive purposes only and cannot be understood as indicating or implying their relative importance or implying the number of technical features indicated. Thus, features defined with "first," "second" may explicitly or implicitly include at least one of such features.

In that present disclosure, unless otherwise specified and defined, the terms "connect," "fix" and the like should be understood broadly, for example, the expression concerning "connect" may be referred to a fixed connection, a detachable connection, or an integral form, may be a mechanical connection or an electrical connection, may be a direct connection or an indirect connection with an intermediate component, may be a communication between interiors of two components or an interaction between two components. For those skilled in the art, the specific meaning of the above terms in the present disclosure may be understood by case. For example, the term "couple" may be broadly understood as any event in which two or more objects are connected in a manner that allows the coupled objects to cooperate with each other without excessive movement therebetween. It should be noted that the coupling may refer to a direct connection, or an indirect connection with several intermediate objects or components. In the description and claims, the terms "couple," "connect," or "engage" may be used interchangeably.

In addition, the technical solutions in the various embodiments of the present disclosure may be combined with each other on the basis of practicability for those skilled in the art. The combination which causes conflicts should be considered as nonexistent and does not fall within the protection scope as claimed by the present disclosure.

With reference to FIGS. 1 to 7, according to the first embodiment of the present disclosure, a strap connector is provided including a core 1, a strap 2 and a pulley 3.

Figures 1, 2:
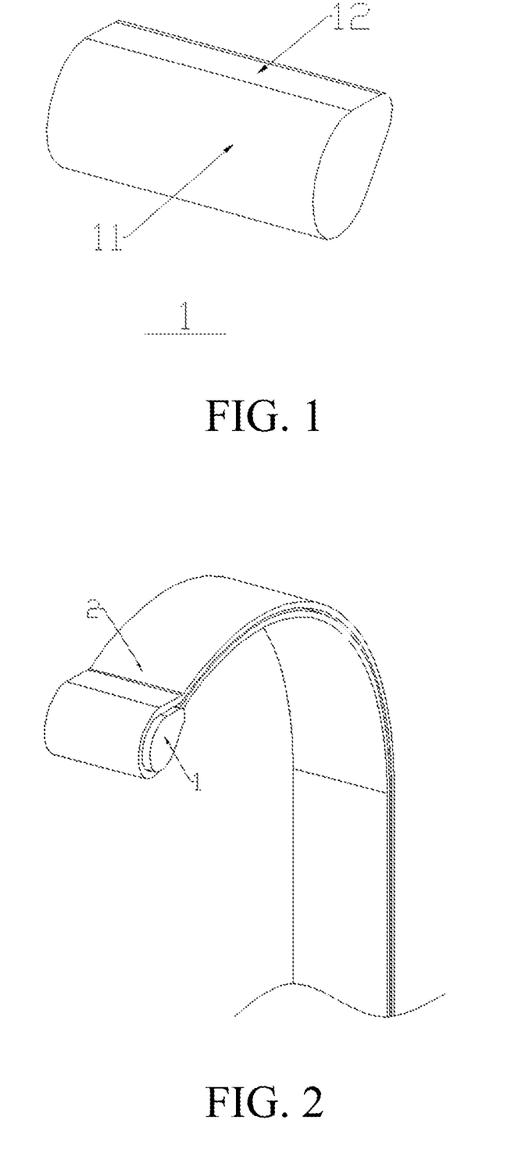
FIG. 1 is a schematic structural diagram of a core according to a first embodiment of the present disclosure.
FIG. 2 is a schematic structural diagram of the core connected with a strap according to the first embodiment of the present disclosure.

As shown in FIG. 1, the core 1 includes a belly portion 11 and a neck portion 12 sized smaller than the belly portion 11. It should be noted that the core 1 is a specific component designed for the strap connector of the present disclosure. The terms such as "core," "belly portion" and "neck portion" are not intended to limit specific shapes of the components as long as the corresponding dimensional relations are satisfied.

As shown in FIG. 2, the strap 2 is connected to the core 1. In this embodiment, the strap 2 is a steel strap. Other strap or rope may be used, for example, a belt which is commonly used as a strap for mechanical transmission. In this embodiment, the strap 2 is connected to the core 1 in such a manner that the strap 2 ride on the belly portion 11 of the core 1 to wrap around the core 1, and both ends of the strap 2 are attached to and extended along the neck portion 12. However, the specific connection between the strap 2 and the core 1 are not limited in the present disclosure. For example, the strap 2 may be coupled to the core 1, or the core 1 and the strap 2 may be integrally formed.

Figure 3:
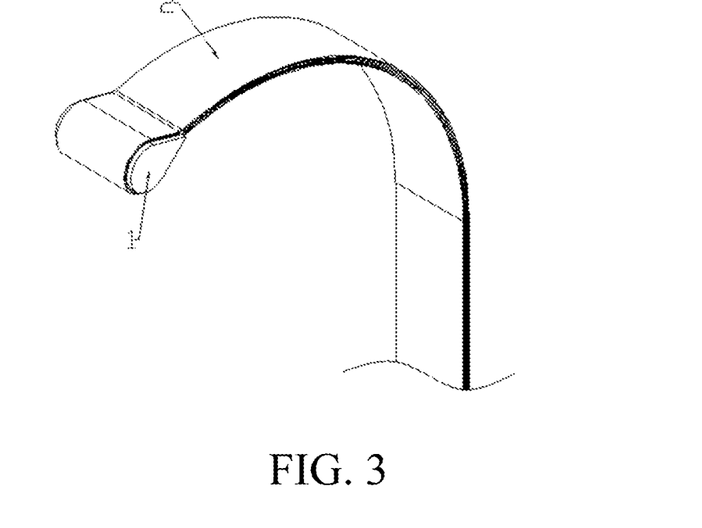
FIG. 3 is a schematic structural diagram of the core connected with a plurality of straps according to the first embodiment of the present disclosure.

In addition, as shown in FIG. 3, the strap 2 may be multi-layered utilizing multiple plies to increase the strength. For example, the strap 2 of two plies wraps around the core 1 and extends further to form a structure of four plies. Specifically, the number of plies in the strap 2 may be designed according to the strength requirements, which is not limited herein.

Figure 4:
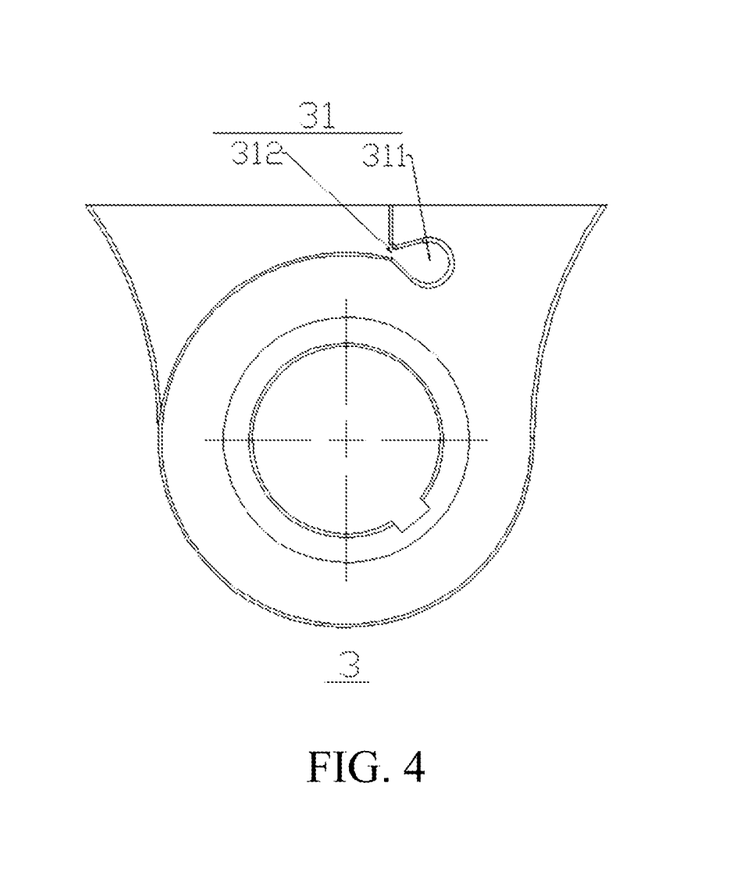
FIG. 4 is a schematic structural diagram of a pulley of the present disclosure.

As shown in FIG. 4, the pulley 3 defines a core chamber 31 which matches the core 1 in shape. The core chamber 31 includes an abdomen 311 and a mouth 312 sized smaller than the abdomen 311. The core chamber 31 at the pulley 3 is specifically designed for the strap connector of the present disclosure, and the specific shapes of the core chamber 31, the abdomen 311 and the mouth 312 may not be limited herein as long as they meet the functional requirements for connection with the core 1 or a connector including the core 1 and the strap 2. Structural designs for other parts of the pulley 3 do not affect the implementation of the present disclosure and thus are not limited herein. For example, structural designs for other parts of the pulley 3 may be the same as or different from those in the existing art.

Figure 5:
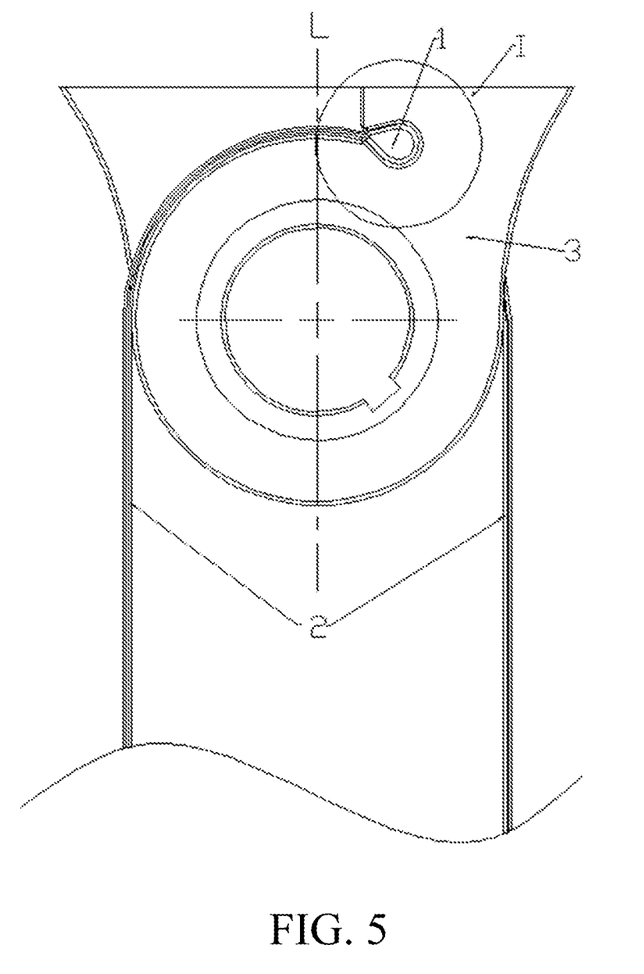
FIG. 5 is a plan view showing a first example of connection of a connector according to the first embodiment of the present disclosure.
Figure 6:
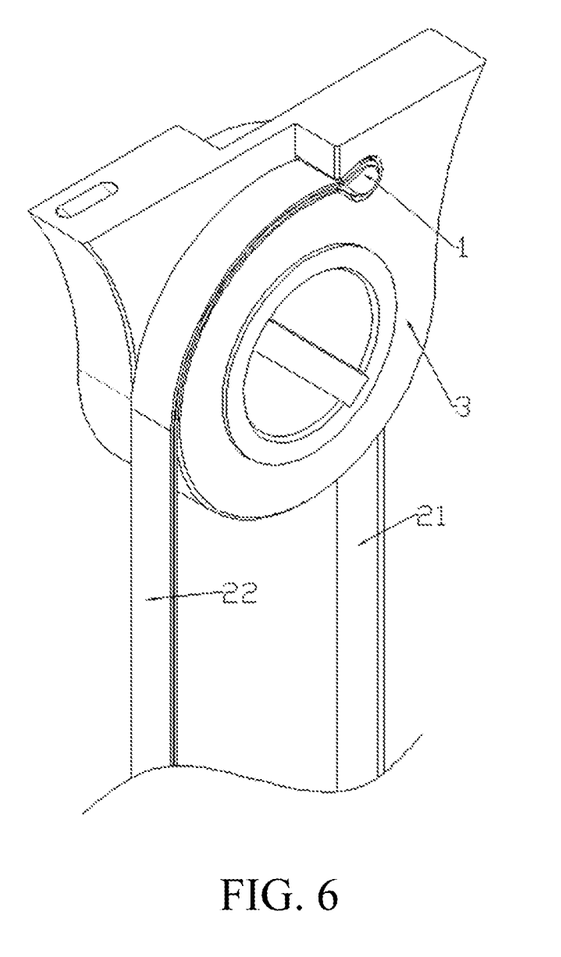
FIG. 6 is a perspective view of a second example of connection of the connector according to the first embodiment of the present disclosure.

As shown in FIGS. 5 and 6, the connector including the core 1 and the strap 2 is connected to the pulley 3 in such a manner that the core 1 is received in the core chamber 31, the belly portion 11 is disposed in the abdomen 311, the neck portion 12 is disposed in the mouth 312, a section size of the belly portion 11 is larger than that of the mouth 312, and the strap 2 extends out of the core chamber 31 through the mouth 312.

In the technical solution of the embodiment, a core 1 with a larger belly portion 11 is provided, and a core chamber 31 with a larger abdomen and a smaller mouth is defined by the pulley 3 and matches the core 1 in shape. The core 1 and the strap 2 are connected and then inserted into the core chamber 31, so that connector can be engaged to the pulley 3. The pulley 3 rotates as the strap 2 runs, thereby realizing transmission.

In this embodiment, both the core 1 and the core chamber 31 are teardrop-shaped. The belly portion 11 has a rear section with a convex surface, and the abdomen 311 has a rear section with a concave surface. The neck portion 12 and the mouth 312 each has a front section tapering in a sharp angle. The belly portion 11 smoothly transitions to the neck portion 12, and the abdomen portion 311 smoothly transitions to the mouth 312. The expression "tapering in a sharp angle" described herein may be understood as tapering to a tip to form a triangle, or may be understood as tapering to form a trapezoid or the like, as long as the neck portion 12 tapers in a direction away from the belly portion 11. In this embodiment, the core 1 is in a shape of a teardrop, the core chamber 31 is teardrop-shaped accordingly, the strap 2 is extended beyond the tip of the teardrop, and the teardrop gets stuck after strap 2 is tensioned, resulting in simple structure, convenient installation, reliable connection.

Figure 7:
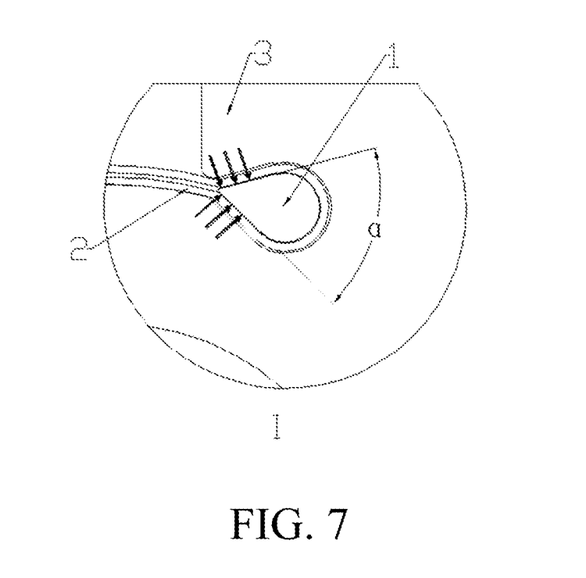
FIG. 7 is a schematic diagram showing a force condition at a position I of the connector according to the first embodiment of the present disclosure.

In the present embodiment, FIG. 7 shows an enlarged view at position I in FIG. 5 (FIG. 7 are simplified in lines for clear illustration) where a force condition is shown. The neck portion 12 has two opposing side surfaces with an angle $\alpha$ of 10° to 60° formed therebetween. With the design of the angle $\alpha$, when the strap 2 is subjected to a pulling force, the belly portion 11 of the core 1 gets stuck in the mouth 312 of the core chamber 31. After the strap 2 is pre-tensioned, the two opposing side surfaces of the neck portion 12 of the core 1 press against inner surfaces of the mouth 312 of the core chamber 31, and a friction on the strap 2 between the pulley 3 and the core 1 due to the pressing forces prevents the strap 2 from moving, thereby reducing a tension stress in a part of the strap 2 at the connector. Directions of the pressing forces of the mouth 1 to the neck portion 12 depend on the design of the angle $\alpha$ which is an included angle formed between the two opposing side surfaces of the neck portion 12 of the core 1. In this way, miniaturization of the strap connector can be achieved for space saving. With a smaller space reserved for connection of the strap 2 and the pulley 3, miniaturization of the corresponding transmission system or the corresponding structure is facilitated.

In the present embodiment, the strap 2 has a section wrapping around the core 1, the core 1 is sized smaller than the core chamber 31 in such a way that both the section of the strap 2 and the core 1 are received in the core chamber 31. With the strap 2 wrapping around the core 1, the upper and lower surfaces of the core 1 are covered by the strap 2, and then both the core 1 and the strap 2 are received in the core chamber 31. The strap 2 mainly suffers from tensile stress, and the tensile yield strength of strap 2 is far higher than the shear yield strength thereof, thereby improving bearing capacity of the strap 2. The strap connector in this embodiment can have its force condition improved at the connection, the strap 2 is not easy to break and may slide slightly within the core chamber 31, so that the internal stress of the strap 2 is fully released, and the service life of the strap 2 is further increased.

In the present embodiment, the strap 2 is a steel strap, and the core 1 is fixed to the steel strap by at least one of welding, gluing and one-time molding of the steel strap through a die. In this way, the steel strap can be smoothly attached to the side surfaces of the core without clearances, and the manufacture and assembly of the strap connector are simple with no welding or slight welding being required, thereby avoiding or reducing stress or deformation of the strap connector caused by welding and thus improving reliability of the strap connector.

Figure 8:
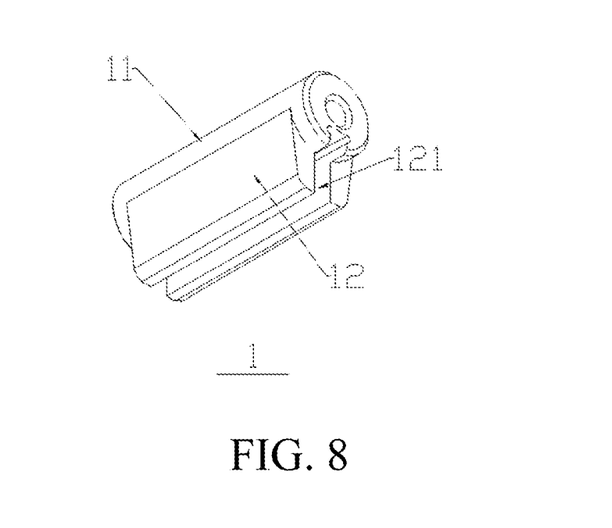
FIG. 8 is a schematic structural diagram of a core according to a second embodiment of the present disclosure.
Figure 9:
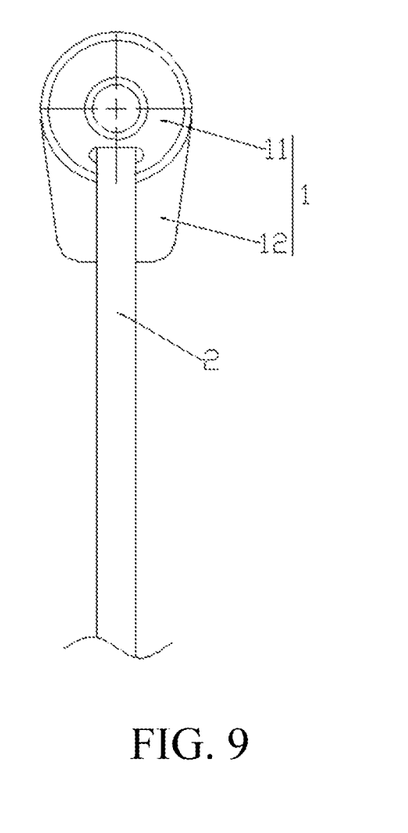
FIG. 9 is a schematic structural diagram of the core connected with a strap according to the second embodiment of the present disclosure.

As shown in FIGS. 8 and 9, the second embodiment is a variant of the first embodiment, and is different from the first embodiment in structure of the core 1. In this embodiment, the neck portion 12 of the core 1 has its middle hollowed to form a strap groove 121 configured to receive and fix the strap 2. The core 1 is inserted into the pulley 3 as described in the first embodiment. When the strap 2 is subjected to a pulling force, the belly portion 11 of the core 1 gets stuck in the mouth 312 of the core chamber 31. The neck portion 12 has two opposing side surfaces with an angle α formed therebetween (not indicated in FIGS. 8 and 9, similar to the first embodiment, specifically an angle between two opposing external surfaces of the neck portion 12), for example, of 10° to 60°. After the strap 2 is pre-tensioned, the two opposing side surfaces of the core 1 press against inner surfaces of the core chamber 31, the pulley 3 compresses the neck portion 2 which in turn compresses the strap 2, and a friction on the strap 2 due to the pressing forces prevent the strap 2 from moving, thereby reducing a tension stress in a part of the strap 2 at the connector. In this embodiment, the belly portion 11 and the neck portion 12 of the core 1 satisfy a corresponding dimensional relation, the neck portion 12 tapers in a direction away from the belly portion 11, and the strap 2 is connected in the middle of the neck portion 12 of the core 1. The strap 2 may be multi-layered utilizing multiple plies to increase the strength. For example, the strap 2 with two to four plies may be used and connected in the middle of the neck portion 12 of the core 1, which is not limited herein. Other technical solutions and effects of this embodiment may be the same as or similar to those of the first embodiment, and will not be repeated herein.

Figure 10:
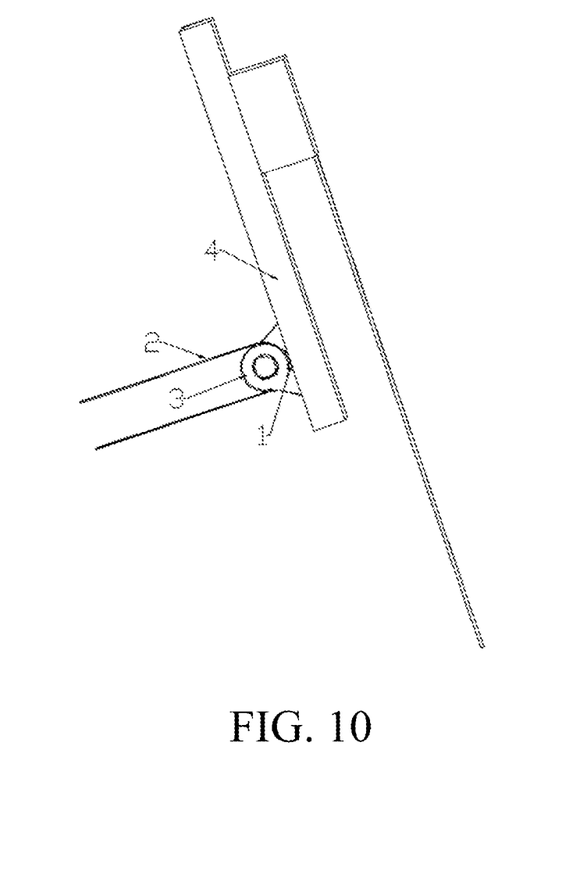
FIG. 10 is a schematic structural diagram showing connection between the connector according to the first embodiment of the present disclosure and a driven unit.
Figure 11:
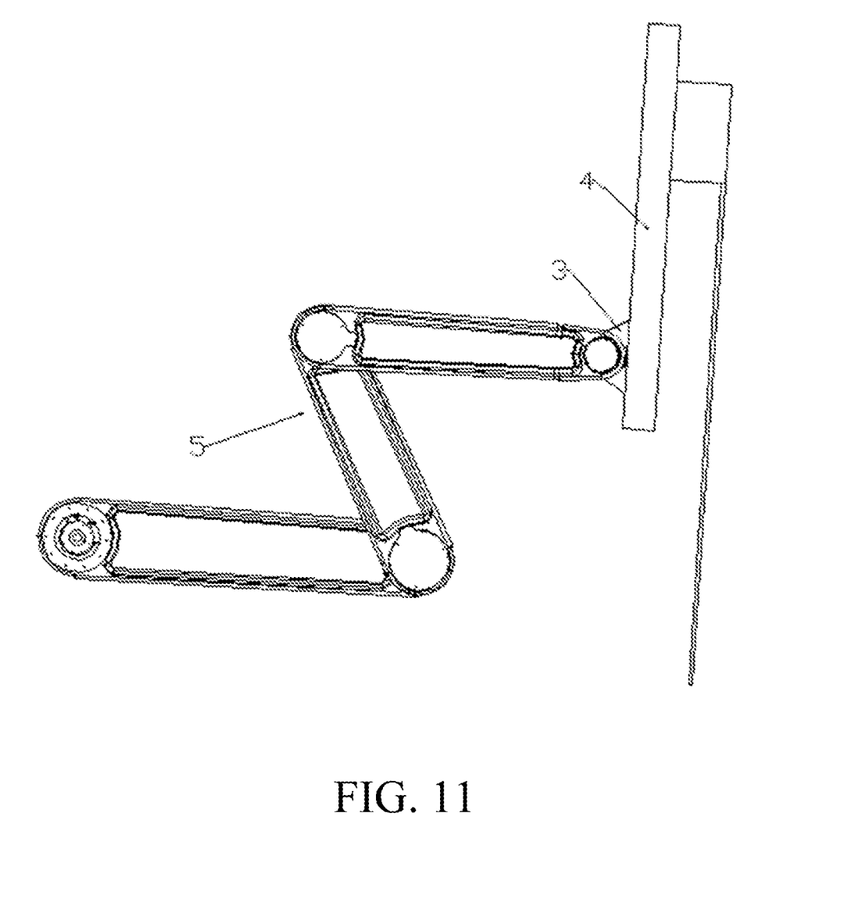
FIG. 11 is a schematic structural diagram of a robotic arm using the connector according to the first embodiment of the present disclosure.

As shown in FIGS. 10 and 11, according to the embodiments of the present disclosure, a robotic arm is provided including serial links and a strap drive train mechanical transmission of serial links. The strap drive train supports the robotic arm and controls the pivoting of the links about the joints connecting the links. The strap drive train runs throughout the robotic arm and includes, in one link of the serial links, a core 1, a strap 2 and a pulley 3. The structures of the core 1, the strap 2 and the pulley 3 as well as the connections therebetween is discussed in the aforementioned embodiments with respect to the strap connector.

Further, as shown in FIGS. 5 and 6, the pulley 3 has a first side and a second side opposing to each other and being rotated-symmetrical about a central axis L of the pulley 3. Each of the first side and the second side is provided with a core chamber 31 receiving a core 1 and a strap 2. The structure and connection on both sides are the same, each employs a core 1 and a core chamber 31 matching each other. The core 1 and a section of the strap 2 are connected to the pulley 3, the strap 2 extends out of the core chamber 31 to ride on the arc profile of the pulley 3 and then further extend to be separated with the peripheral surface of the pulley 3. In this way, the strap 2 and the pulley 3 at an end of the robotic arm are connected. With the two opposing sides of the pulley 3 being rotated-symmetrical and each of which being provided with a respective core chamber 31 receiving a core 1 and a strap 2, the strap 2 drives the pulley 3 to rotate clockwise or anticlockwise. In a case where the pulley 3 is connected to a driven unit 4 shown in FIG. 10 (for example, the driven unit 4 may be an end link which serves as an instrument holder), the driven unit 4 pitches as the pulley 3 rotates. The arc-shaped portion of the pulley 3 and other structural features may be the same as or similar to those in the existing art, for example, a pulley connected to an end link of the existing surgical robot, or may be modified on the basis of the existing structure, as long as the functional requirements of the pulley 3 are met.

Further, the strap 2 may be connected in at least two manners. For example, as shown in FIG. 5, one strap 2 is provided and has a first end, a second end and a middle section. The first end is connected to a first core 1 and received in a first core chamber 31 at a first side of the pulley 3, the second end is connected to a second core 1 and received in a second core chamber 31 at a second side of the pulley 3, and the middle section is connected to another end of the robotic arm (for example, an end of the arm connected to the drive unit 5 as shown in FIG. 11). The middle section of the strap 2 may wrap around a pulley of another structure or may be connected to another structure in other manners, which is not limited herein. For another example, a plurality of straps 2 are provided, such as two straps 2 as shown in FIG. 6, namely, a first strap 21 and a second strap 22. Each of the two straps 2 has a first end and a second end. The first end is connected to a respective core 1 and received in a respective core chamber 31 at a respective one of the first side and the second side of the pulley 3, and the second end is connected to another end of the robotic arm (for example, an end of the arm connected to the drive unit 5 as shown in FIG. 11). The structure and connection at the other end of the robotic arm may be the same as or different from those as described above, which is not limited herein.

According to the embodiments of the present disclosure, a robot including a robotic arm as described in any one of the above embodiments. In the robot, a transmission control of an end link of the robotic arm is achieved through the strap drive train (as shown in FIGS. 10 and 11), so that the end link of the robotic arm is operable for surgery.

The robotic arm and the robot employ the core 1, the strap 2 and the pulley 3 as discussed in the aforementioned embodiments with respect to the strap connector, and thus have at least all the technical effects of the above embodiments, which are not repeated herein.

In addition, although the embodiments of the present disclosure are described with respect to a robotic arm applied to a surgical robot, it should be appreciated by those skilled in the art that besides the application scenario discussed in the present disclosure, technical solutions provided in the present disclosure are widely applicable to the field of mechanical transmission.

The description above is merely some embodiments of the present disclosure, and is not intended to limit the scope of the present disclosure. Any equivalent structural transformation made using the contents of the specification and drawings of the present disclosure or applied in other related technical fields under the concept of the present disclosure falls within the scope of the present disclosure.

What is claimed is:

1. A strap connector, comprising:
a core including a belly portion and a neck portion fixed to the belly portion, the neck portion having a width tapering in a direction away from the belly portion;
a pulley defining a core chamber in which the core is received, the core chamber being accessible through an opening; and
a strap connected to the core and extending out of the core chamber through the opening;
wherein the core chamber has two inner side walls opposing each other and extending from the opening, the neck portion is disposed closer to the opening than the belly portion, the neck portion and the strap are sandwiched between the two inner walls of the core chamber.

2. The strap connector according to claim 1, wherein the neck portion has two side surfaces facing away from each other and extending closer to each other as the neck portion tapers, the two inner walls of the core chamber press the two side surfaces when the strap is tensioned.

3. The strap connector according to claim 2, wherein the neck portion of the core defines a strap groove at a middle of the neck portion, the strap groove opens to and communicates with the opening of the core chamber, the strap has a section received and fixed in the strap groove, and the two inner walls of the core chamber abuts against the two side surfaces of the neck portion which in turn clamps the strap when the strap is tensioned.

4. The strap connector according to claim 2, wherein the core chamber further has a bottom wall with a concave surface opposing to the opening, and the neck portion has a convex surface connecting the two side surfaces and facing the concave surface.

5. The strap connector according to claim 2, wherein a clearance is formed between the core and the core chamber and along a periphery of the core, the strap has a section wrapping the core and disposed in the clearance, the two inner walls of the core chamber press the strap against the two side surfaces of the neck portion when the strap is tensioned.

6. The strap connector according to claim 5, wherein the strap includes a steel strap, the core is fixed to the steel strap by at least one of welding, gluing and one-time molding of the steel strap through a die.

7. The strap connector according to claim 2, wherein an angle between the two side surfaces of the neck portion is in a range of 10° to 60°.

8. The strap connector according to claim 1, wherein the strap has a section received within the core chamber and connected to the core, and both ends of the section extend out of the core chamber through the opening.

9. The strap connector according to claim 8, wherein the section wraps the core.

10. The strap connector according to claim 8, wherein the neck portion of the core defines a strap groove, and the section is partly received within the strap groove.

11. The strap connector according to claim 8, wherein both ends of the section are pulled upon tensioning of the strap.

12. The strap connector according to claim 1, wherein the strap is folded to form two layers, the two layers ride on the pulley and end up with attachment to the core.

13. The strap connector according to claim 12, wherein a friction is formed between the core and each of the two layers upon tensioning of the strap.

14. The strap connector according to claim 12, wherein the neck portion has a flat surface contacting one of the two layers, and a friction is formed between the flat surface and the one of the two layers upon tensioning of the strap.

15. The strap connector according to claim 1, wherein the core chamber has a tapered space defined by the two inner side walls, the tapered space tapers towards the opening, the neck portion and the strap are tightly fitted into the tapered space upon tensioning of the strap.

16. A robotic arm comprising serial links and a strap drive train for mechanical transmission of serial links, wherein the strap drive train in one link of the serial links includes:
a core including a belly portion and a neck portion fixed to the belly portion, the neck portion having a width tapering in a direction away from the belly portion;
a pulley disposed at one end of the link and defining a core chamber in which the core is received, the core chamber being accessible through an opening; and
a strap connected to the core and extending out of the core chamber through the opening;
wherein the core chamber has two inner side walls opposing each other and extending from the opening, the neck portion is disposed closer to the opening than the belly portion, the neck portion and the strap are sandwiched between the two inner walls of the core chamber.

17. The robotic arm according to claim 16, wherein the pulley has a first side and a second side opposing to each other and being rotated-symmetrical, and each of the first side and the second side is provided with a core chamber receiving a core and a strap.

18. The robotic arm according to claim 17, wherein one strap is provided and has a first end, a second end and a middle section, the first end is connected to a first core and received in a first core chamber at the first side of the pulley, the second end is connected to a second core and received in a second core chamber at the second side of the pulley, and the middle section is connected to one other end of the link.

19. The robotic arm according to claim 17, wherein two straps are provided, each of the two straps has a first end and a second end, the first end is connected to a respective core and received in a respective core chamber at a respective one of the first side and the second side of the pulley, and the second end is connected to one other end of the link.

20. A robot comprising a robotic arm, wherein the robotic arm includes serial links and a strap drive train for mechanical transmission of serial links, and the strap drive train in one link of the serial links includes:
a core including a belly portion and a neck portion fixed to the belly portion, the neck portion having a width tapering in a direction away from the belly portion;

a pulley disposed at one end of the link and defining a core chamber in which the core is received, the core chamber being accessible through an opening; and a strap connected to the core and extending out of the core chamber through the opening;

wherein the core chamber has two inner side walls opposing each other and extending from the opening, the neck portion is disposed closer to the opening than the belly portion, the neck portion and the strap are sandwiched between the two inner walls of the core chamber.

* * * * *